(12) United States Patent
Lee et al.

(10) Patent No.: US 7,392,719 B2
(45) Date of Patent: Jul. 1, 2008

(54) DEVICES AND METHODS FOR SAMPLING GROUNDWATER

(75) Inventors: Bong Joo Lee, Daejeon (KR); Tae Hee Kim, Daejeon (KR); Yong Je Kim, Daejeon (KR)

(73) Assignee: Korea Institute of Geoscience and Mineral Resources (KR)

( * ) Notice: Subject to any disclaimer, the term of this patent is extended or adjusted under 35 U.S.C. 154(b) by 387 days.

(21) Appl. No.: 11/201,034

(22) Filed: Aug. 10, 2005

(65) Prior Publication Data
US 2006/0107770 A1      May 25, 2006

(30) Foreign Application Priority Data
Nov. 19, 2004 (KR) .................. 10-2004-0094855

(51) Int. Cl.
*E21B 49/08* (2006.01)
*G01N 1/16* (2006.01)

(52) U.S. Cl. ............... 73/863.31; 73/864.66; 73/864.67; 175/308; 166/264; 166/165

(58) Field of Classification Search ............. 73/863.31, 73/864.63, 864.66–864.67; 175/308, 50; 166/264, 165
See application file for complete search history.

(56) References Cited

U.S. PATENT DOCUMENTS

| 4,438,654 | A | * | 3/1984 | Torstensson | ............ 166/264 X |
| 4,884,439 | A | * | 12/1989 | Baird | .................. 166/264 X |
| 4,940,088 | A | * | 7/1990 | Goldschild | ............. 166/264 X |
| 5,520,046 | A | * | 5/1996 | Sornein et al. | .......... 166/264 X |
| 5,662,166 | A |   | 9/1997 | Shammai | |
| 6,557,632 | B2 |   | 5/2003 | Cernosek | |
| 7,178,415 | B2 | * | 2/2007 | Britt | ........................ 73/864.67 |

FOREIGN PATENT DOCUMENTS

KR     10-2004-0046802     6/2004

* cited by examiner

*Primary Examiner*—Thomas P Noland
(74) *Attorney, Agent, or Firm*—Michael Best & Friedrich

(57) ABSTRACT

Some embodiments of the present invention are related to devices and methods for sampling groundwater at multiple target depths, wherein each of the devices for sampling groundwater at multiple target depths comprises: a hammer part having a spring for generating inertia and a hammer connected to the spring; a sampling needle part having a needle integral with a impacting part impacted with the hammer; a guiding part for moving the sampling needle part in straight and downward direction; and a sampled water containing part having a sampled water container for collecting the sampled water through the needle.

17 Claims, 13 Drawing Sheets

DEVICES AND METHODS FOR SAMPLING GROUNDWATER

TECHNICAL FIELD

The present invention relates to devices and methods for sampling groundwater, including devices and methods for sampling groundwater at multiple target depths.

BACKGROUND ART

Demand continues to increase for devices capable of obtaining a representative sample of water at a target depth, and for determining a water-sampling depth through a thorough analysis in a vertical groundwater flow pattern in a borehole when analyzing the quality of the groundwater.

Water samplers conventionally used include suction lift pumps, down-well centrifugal pumps, multi-level down-well sampling systems and passive diffusional samplers. Samplers using a pump may disturb the vertical flow of groundwater, thereby negatively impacting the accuracy of the samplers. In the case of passive diffusional samplers, an advantage exists in that groundwater flow disturbance does not occur. However, a shortcoming of passive diffusional samplers is that a week is required to sample groundwater. In the case of grab sampling devices (the most conventional type of which is a bailer), the possibility of flow disturbance is low by instantaneous groundwater sampling in a borehole, although there is a shortcoming that the depth of sampling cannot be specified.

DISCLOSURE OF THE INVENTION

Therefore, an object of some embodiments of the present invention is to solve the problems found in the prior art, to provide a device capable of taking advantage of the merits of the grab sampling device while controlling a depth for sampling groundwater, and while sampling groundwater at multiple target depths without a driving source (such as an electrical or pneumatic driving source). More particularly, the object of some embodiments of the present invention is to provide devices and methods for sampling groundwater at multiple target depths, wherein a discrete device is installed in the groundwater in a borehole and is positioned at a target depth, a needle is penetrated through a packing in a sampling tub by inertia generated from remote-controlled human power without any driving source on the ground, and the needle acts as a inflow passage for sampling water filling the sampling tub from the target depth.

BRIEF DESCRIPTION OF THE DRAWINGS

The above objects, and other features and advantages of the present invention will become more apparent by describing the preferred embodiment thereof with reference to the accompanying drawings, in which.

BRIEF DESCRIPTION OF NUMBERS USED IN THE FIGURES

| | |
|---|---|
| 1: An upper connecting ring | 2: A position adjusting bolt |
| 3: A position adjusting screw | 4: A spring |
| 5: A hammer | 6: An impacting part |
| 7: An upper suction hole | 8: A side suction hole |
| 9: A needle | 10: A needle guide |
| 11: A guide locking portion | 12: A packing |
| 13: A submerging part | 14: A sampled water container |
| 15: A lower connecting ring | 16: A passage for sampling |
| 17: A guide | 18: A hammer casing |
| 19: A passage for sampling | 20: A casing for sampling needle part |
| 40: A hammer part | 45: A sampling needle part |
| 50: A guiding part | 60: A sampled water containing part |

DETAILED DESCRIPTION

Reference will now be made in detail to a device for discrete interval groundwater sampling according to an embodiment of the present invention using the accompanying Figures.

Figure 1:
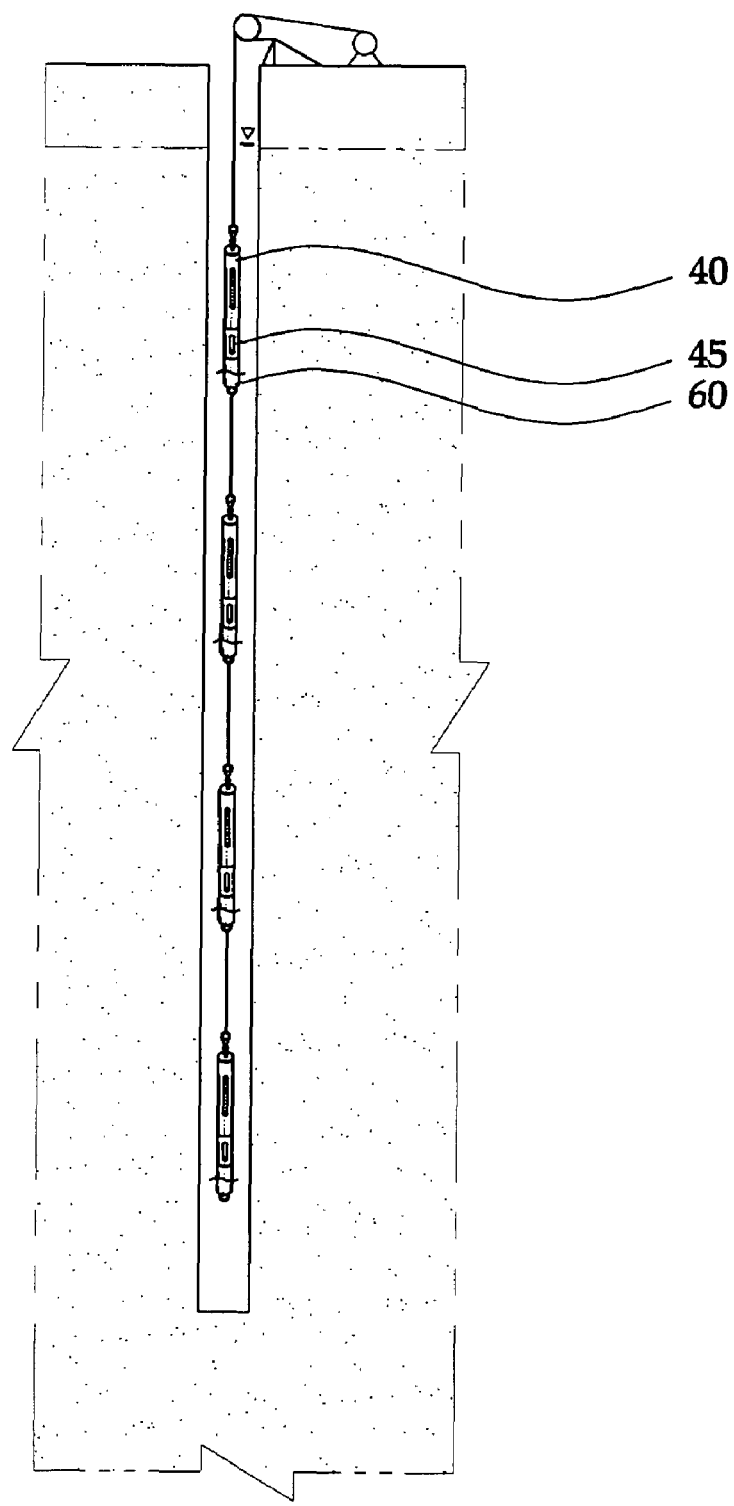
FIG. 1 is a schematic diagram showing installation of devices for sampling groundwater at multiple target depths according to the present invention.
Figure 2A:
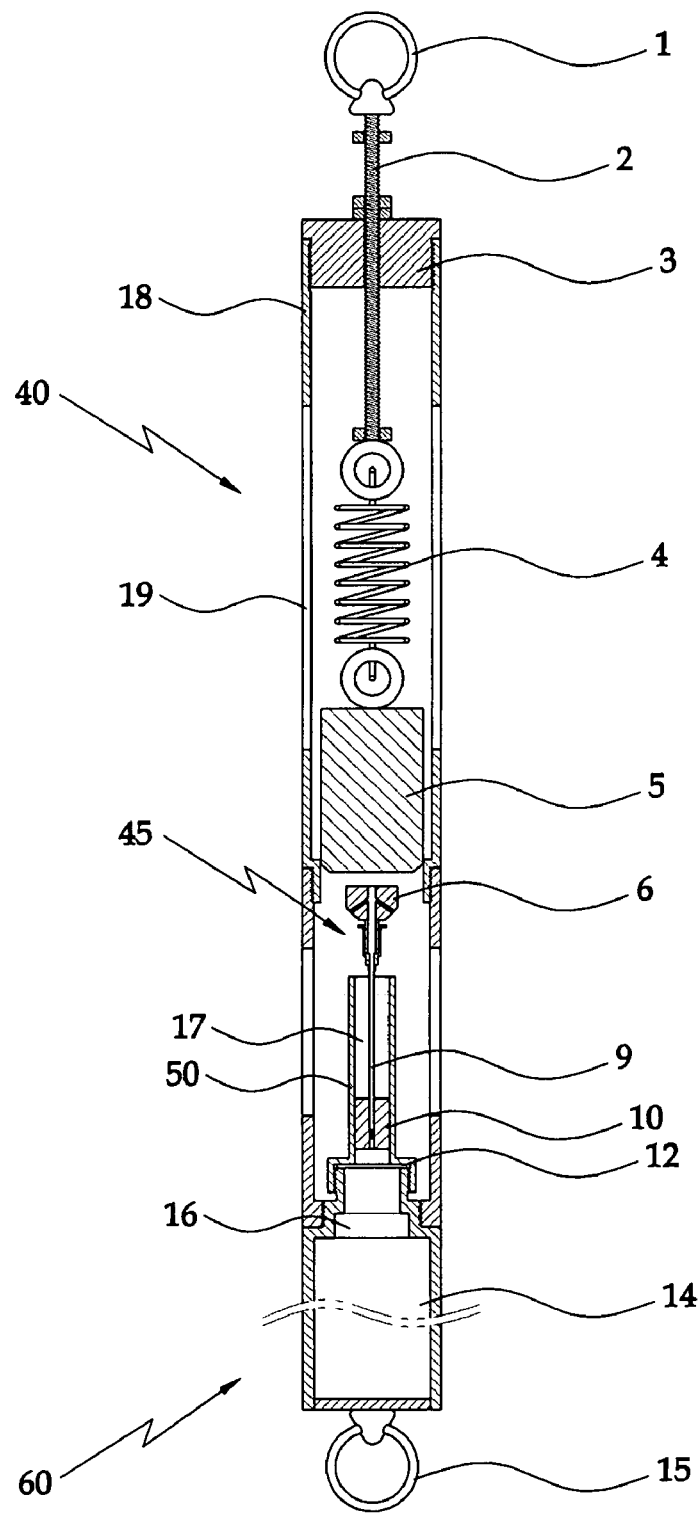
FIG. 2a is a schematic diagram showing the state of a discrete groundwater sampling device according to an embodiment of the present invention before operation of the device.
Figure 2B:
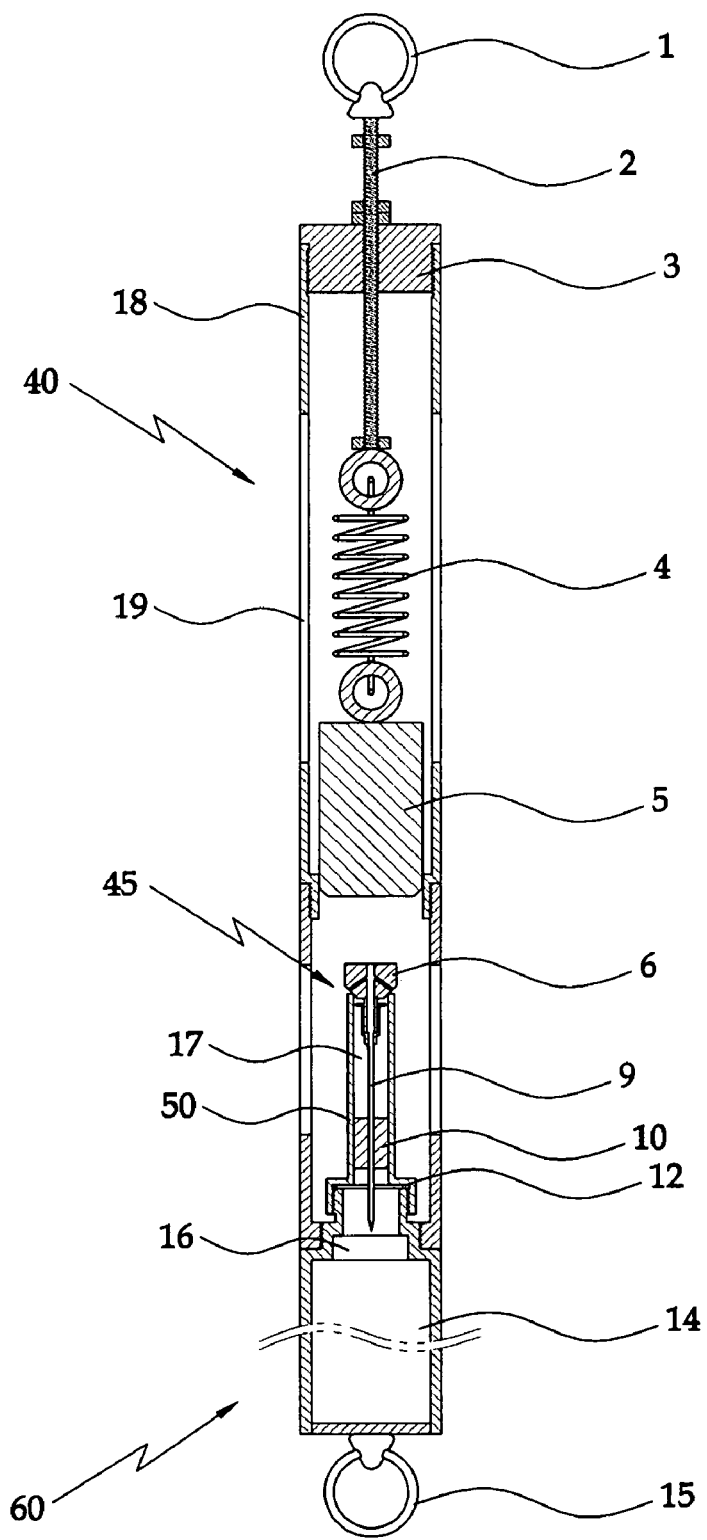
FIG. 2b is a schematic diagram showing the state of a discrete groundwater sampling device according to an embodiment of the present invention after operation of the device.
Figure 3:
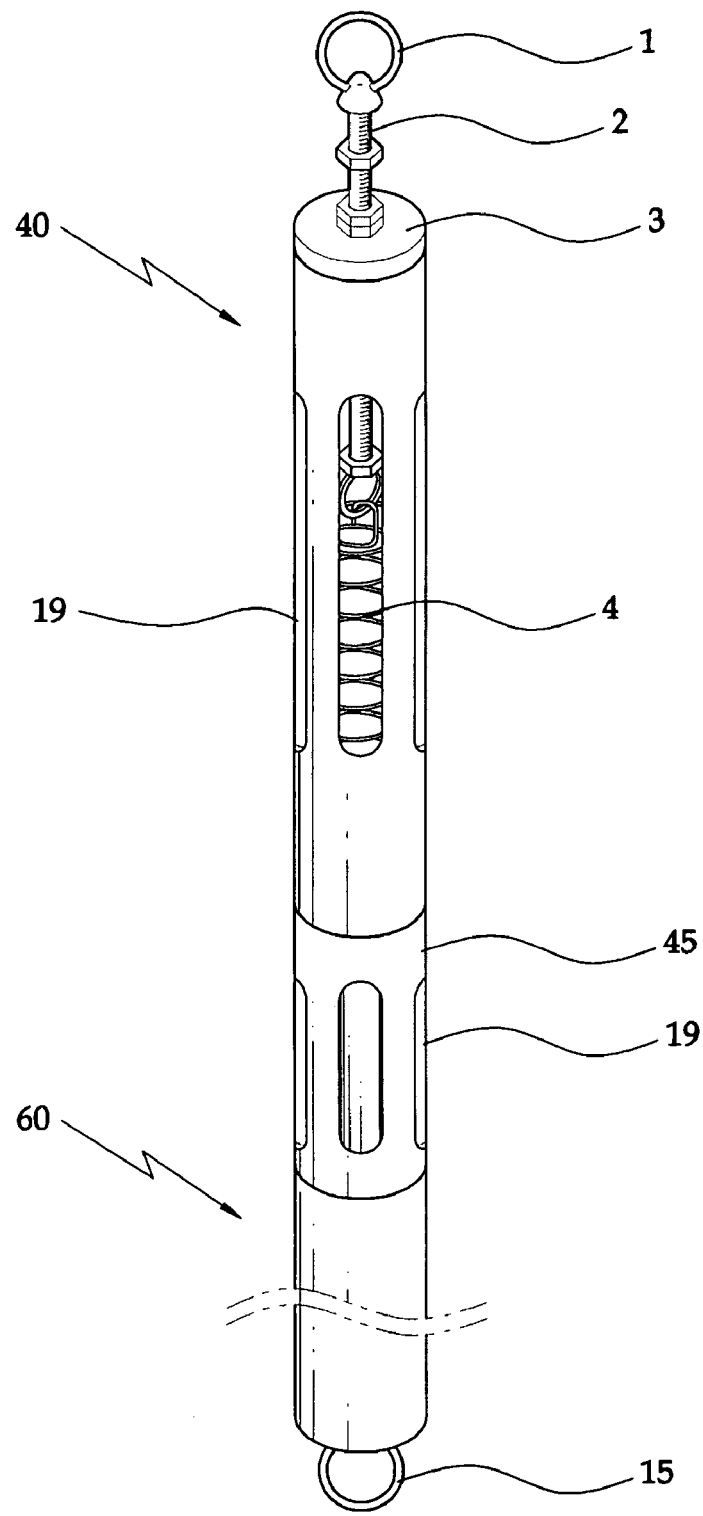
FIG. 3 is a perspective view of an assembled discrete device for sampling groundwater at multiple target depths according to an embodiment of the present invention.

FIG. 1 is a schematic diagram showing installation of devices sampling groundwater at multiple target depths according to an embodiment of the present invention. FIG. 2a is a schematic diagram showing a state of a discrete device for sampling groundwater at multiple target depths according to the present invention, shown before operation. FIG. 2a is a schematic diagram showing a state of a discrete device for sampling groundwater at multiple target depths according to the present invention, shown after operation. FIG. 3 is a perspective view of an assembled discrete device for sampling groundwater at multiple target depths according to an embodiment of the present invention. In the figures, each of the illustrated devices for sampling groundwater at multiple target depths according to the present invention comprises: a hammer part 40 having a spring 4 for generating inertia and a hammer 5 connected to the spring; a sampling needle part 45 having a needle 9 integral with an impacting part 6 impacted with the hammer 5; a guiding part 50 for moving the sampling needle part 45 in a straight and downward direction; and a sampled water containing part 6 having a sampled water container 14 for collecting sampled water flowing through the needle 9.

Figure 4:
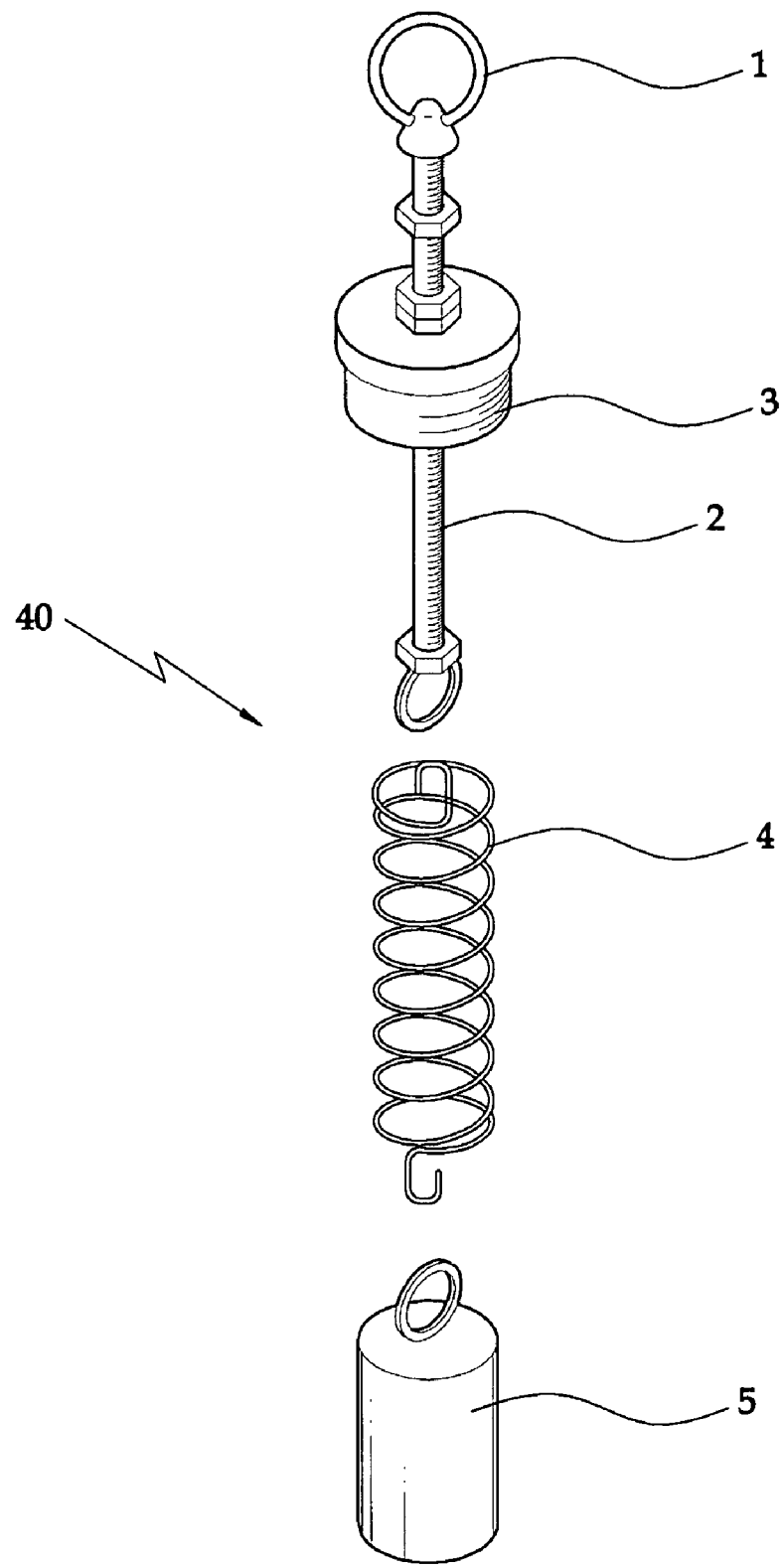
FIG. 4 is a perspective view of a hammer part according to an embodiment of the present invention.

FIG. 4 is a perspective view of a hammer part 40 according to an embodiment of the present invention. The hammer part 40 comprises a screw 3 for adjusting a position of a spring 4 and a hammer 5 coupled to a position adjusting bolt 2. The spring 4 is connected to the lower end of the position adjusting bolt 2, and the hammer 5 is connected to the lower end of the spring 4. An upper connecting ring 1 is mounted on the upper end of the hammer part 40.

Figure 5:
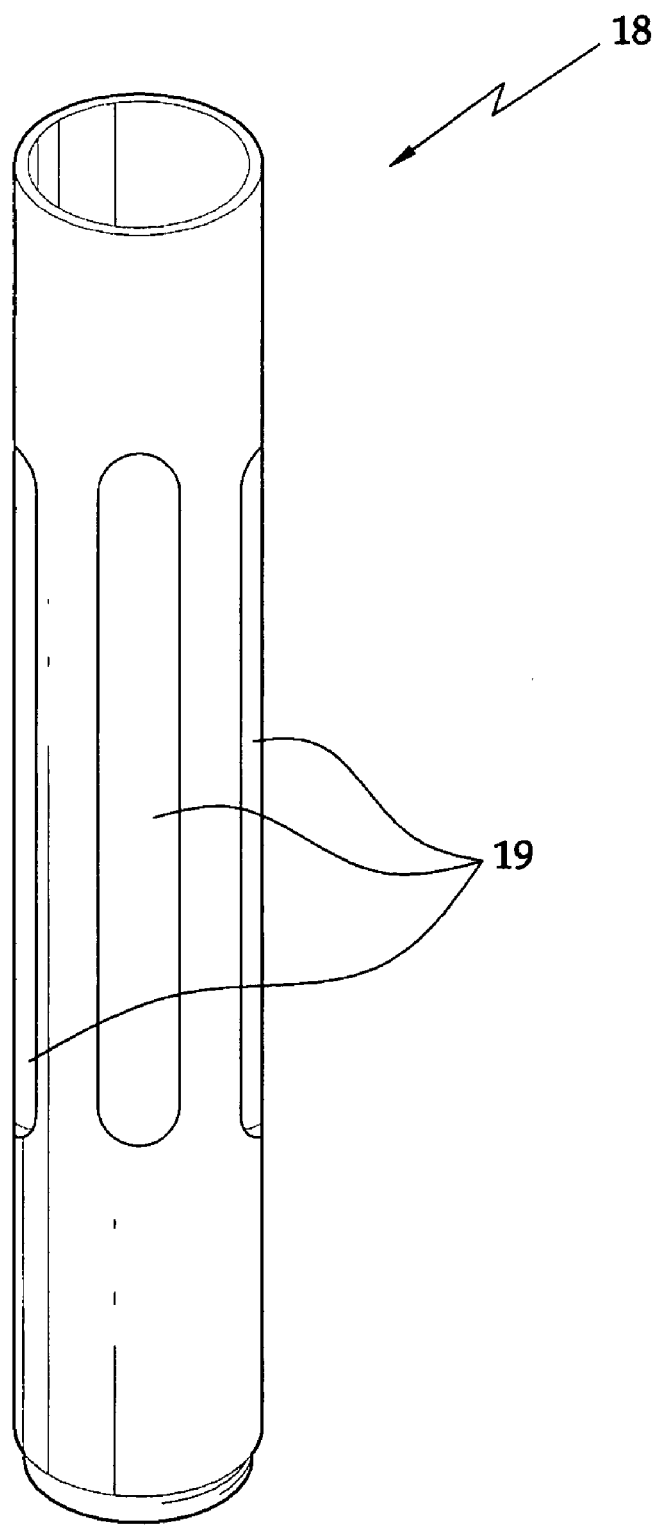
FIG. 5 is a perspective view of a hammer casing according to an embodiment of the present invention.

FIG. 5 is a perspective view of a hammer casing 18 according to an embodiment of the present invention. The inner part of the hammer casing 18 is shaped as a tube to position the hammer part 40 therein and to protect the hammer part 40. Two or more passages 19 for sampling are formed in the circumference of the hammer casing 18. With the hammer casing 18 in such an arrangement, the hammer moves freely in upward and downward directions as groundwater flows freely into and out of the hammer casing 18, thereby minimizing resistance by the groundwater.

Figure 6:
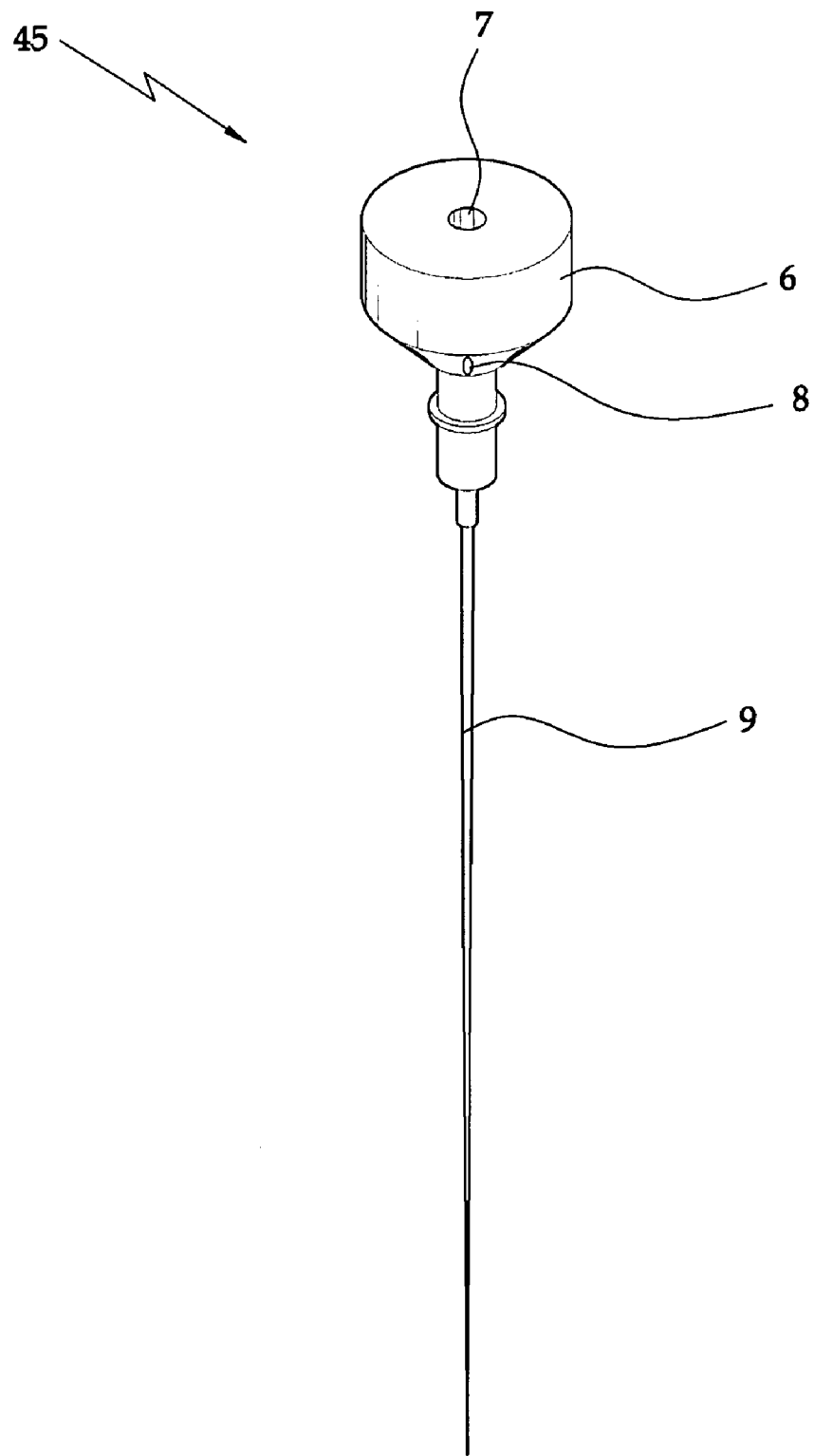
FIG. 6 is a perspective view of a sampling needle part according to an embodiment of the present invention.

FIG. 6 is a perspective view of a sampling needle part according to an embodiment of the present invention. The sampling needle part 45 comprises: an upper suction hole 7 formed on an impacting part 6 impacted with the hammer 5; a side suction hole 8 formed on a side of the impacting part 6 and in communication with the upper suction hole 7; and a needle 9 formed vertically on a surface on which the side suction hole 8 and the upper suction hole 7 communicate with one another.

The sampling needle part 45 is moved downwardly when impacted by the hammer 5, and penetrates a rubber packing 12 (described below) of a sampled water containing part 60 (also described below). Thereafter, the needle 9 penetrating the rubber packing 12 of the sampled water containing part 60 acts as a passage through which groundwater is sucked through the upper and side suction holes 7 and 8 on the impacting part 6 and into the sampled water containing part 60.

Figure 7:
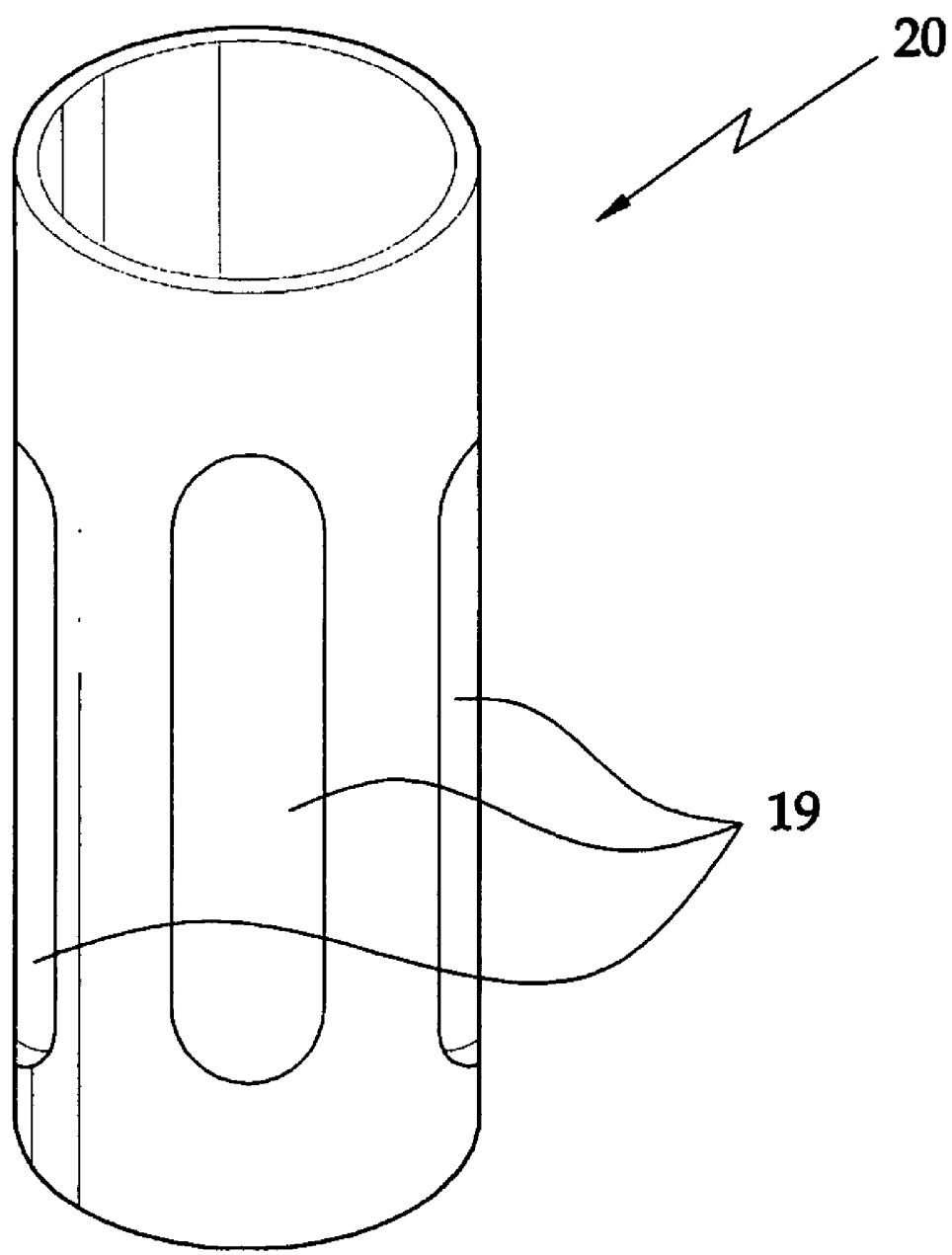
FIG. 7 is a perspective view of a casing for a sampling needle part according to an embodiment of the present invention.

FIG. 7 is a perspective view of a casing 20 for the sampling needle part 45 according to an embodiment of the present invention. The casing 20 for the sampling needle part 45 is shaped as a tube to be installed on the lower end of the hammer casing 18, protects the sampling needle part 45 by positioning the sampling needle part therein, and has one and more passages 19 for sampling formed on the circumference thereof in order for surrounding groundwater to flow therethrough.

Figure 8:
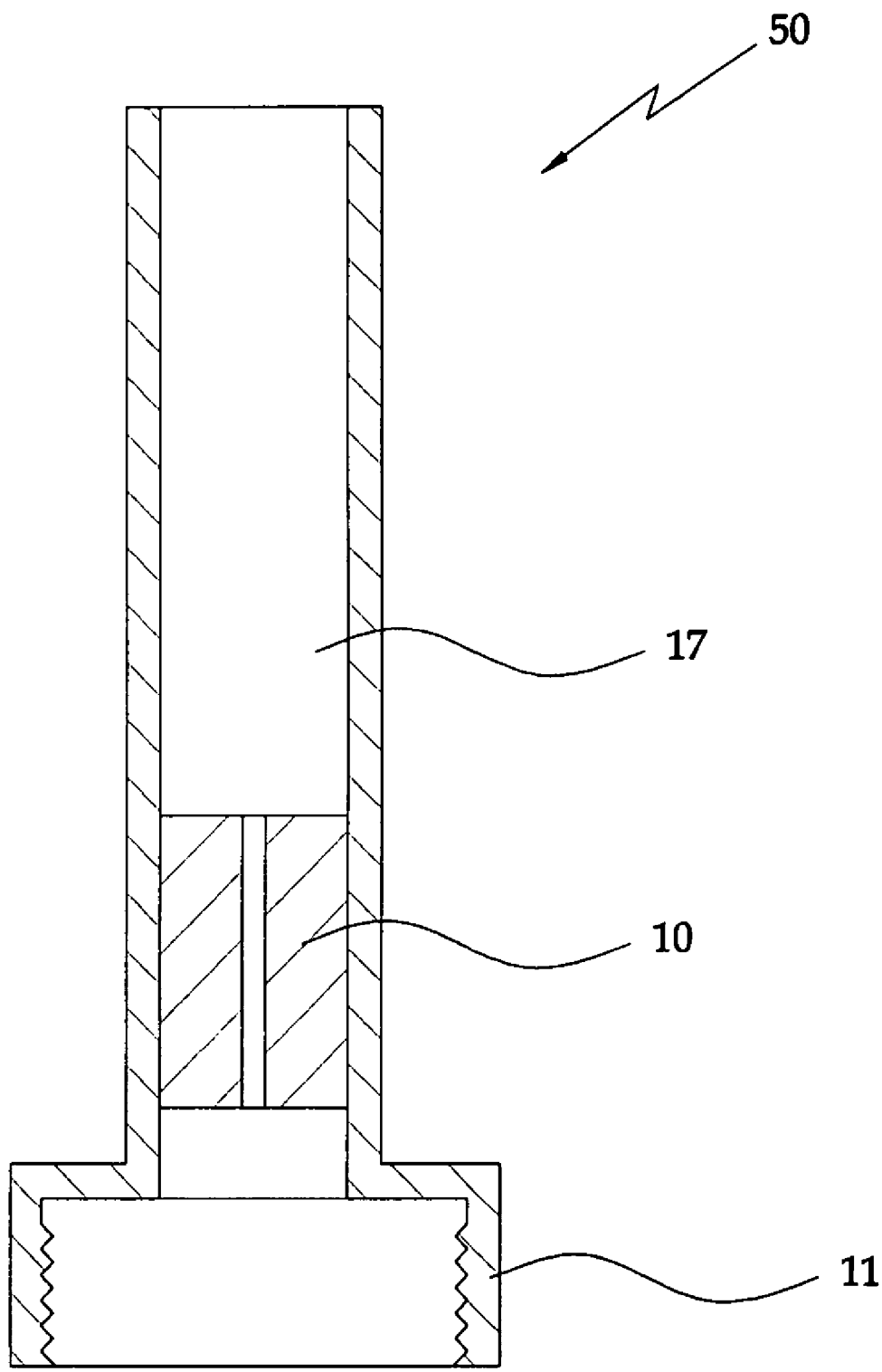
FIG. 8 is a schematic view of a guiding part according to an embodiment of the present invention.

FIG. 8 is a schematic view showing a guiding part according to an embodiment of the present invention. The guiding part 50 is comprised of a guide 17 shaped as a tube, a needle guide 10 which is positioned on the lower end of the guide 17 and conducts vertical downward movement of the needle 9, and a guide locking portion 11. The guide locking portion 11 is for adjusting the degree that the needle 9 penetrates through the rubber packing 12.

Figure 9:
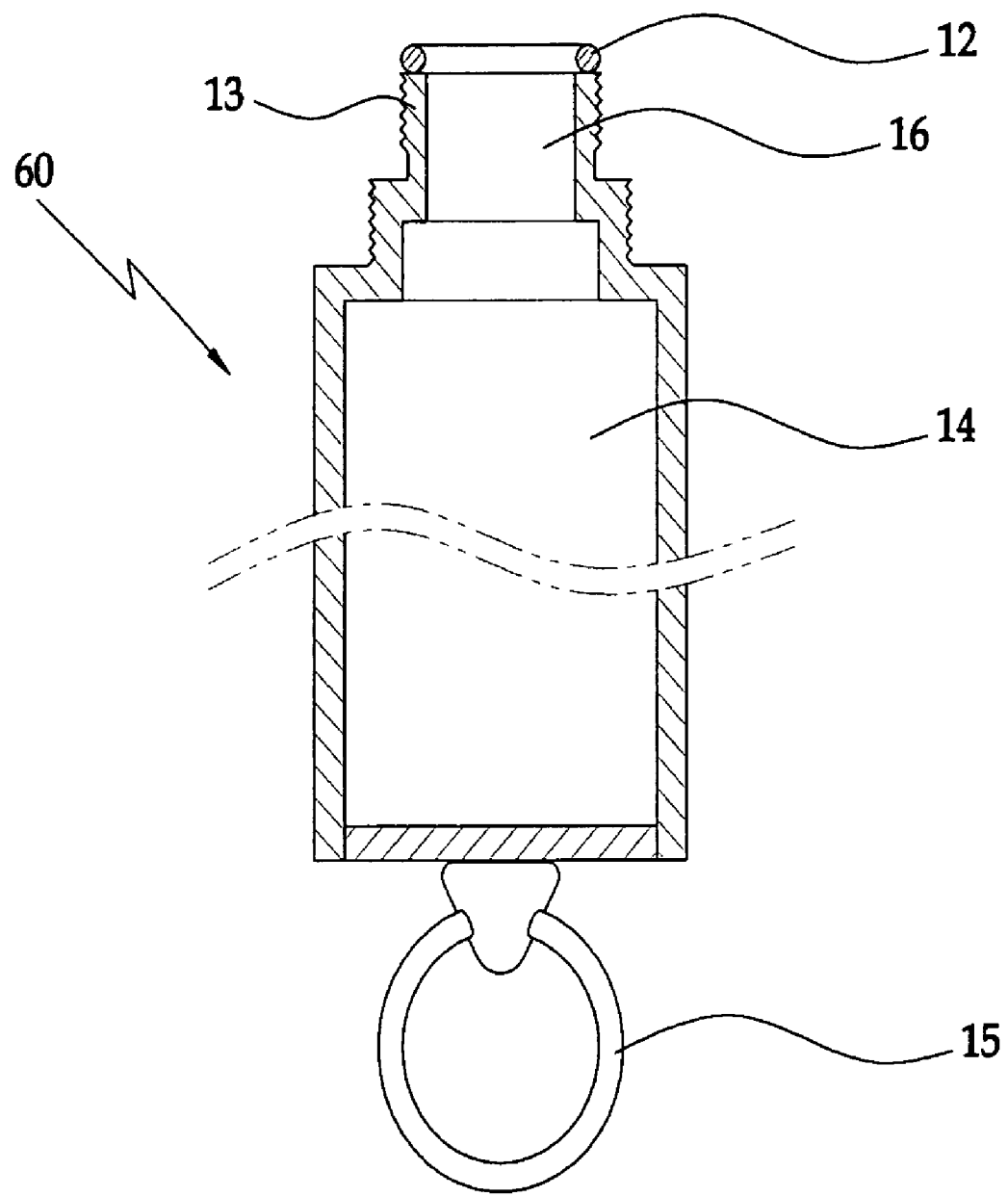
FIG. 9 is a schematic view of a sampled water containing part according to an embodiment of the present invention.

FIG. 9 is a schematic view showing a sampled water containing part 60 according to an embodiment of the present invention. In FIG. 9, the sampled water containing part 60 includes a hollow submerging part 13 for sampling ground water which corresponds to the guide locking portion 11 of the guiding part 50; a packing part 12 mounted on the upper end of the submerging part 13; and a sampled water container 14 which is for containing a sample of groundwater and is connected to the lower end of the submerging part 13.

The packing part 12 is made of a rubber having elasticity, and is formed to entirely close the sampled water containing part 60. A lower connecting ring 15 is attached to the lower end of the sampled water containing part 60 to connect with any other device (e.g., by means of a wire, such as a steel wire) under the sampled water containing part 60 for discrete interval groundwater sampling.

Figure 10:
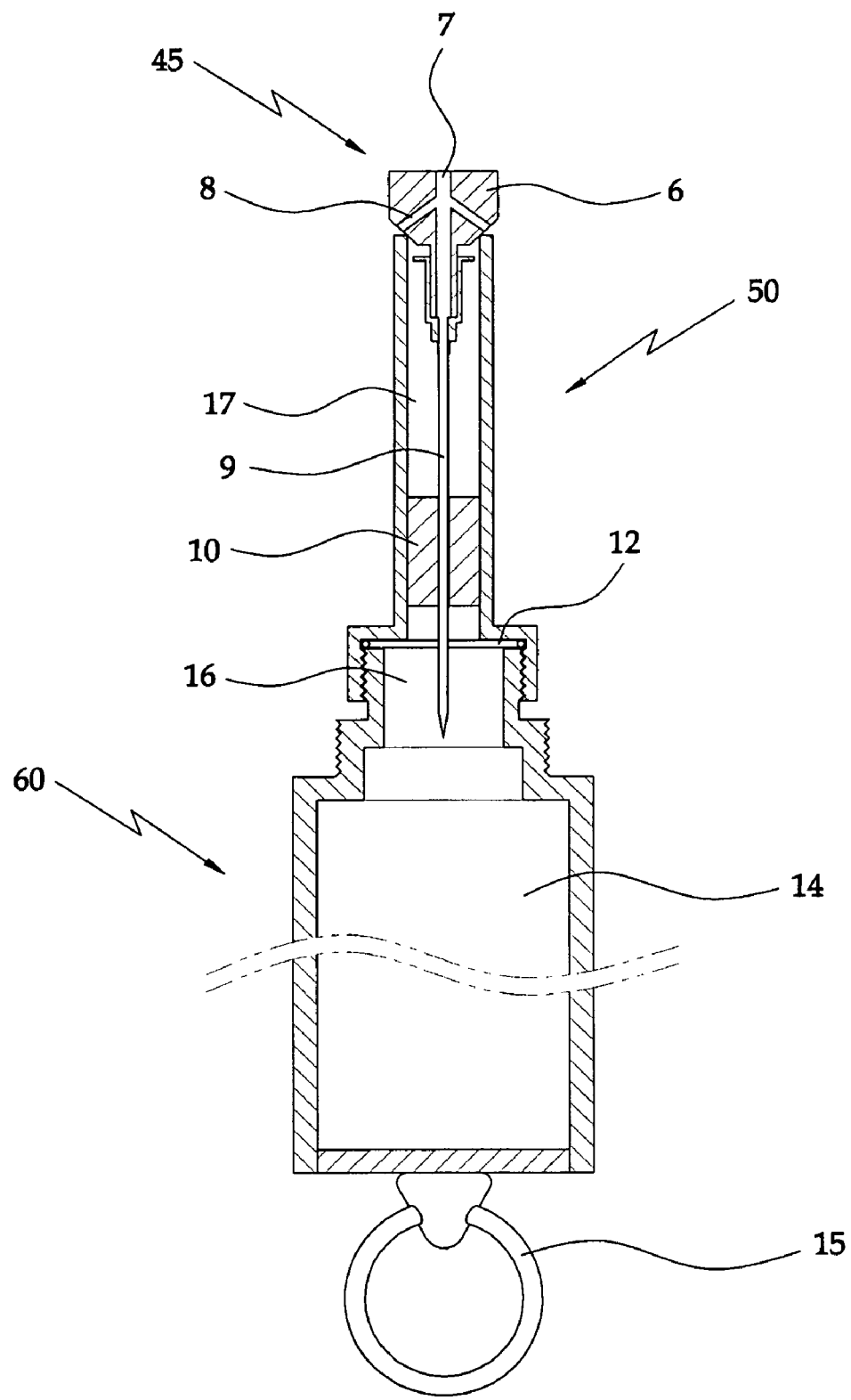
FIG. 10 is a schematic view showing an assembled sate of the sampling needle part, the guiding part and the sampled water containing part according to an embodiment of the present invention.
Figure 11A:
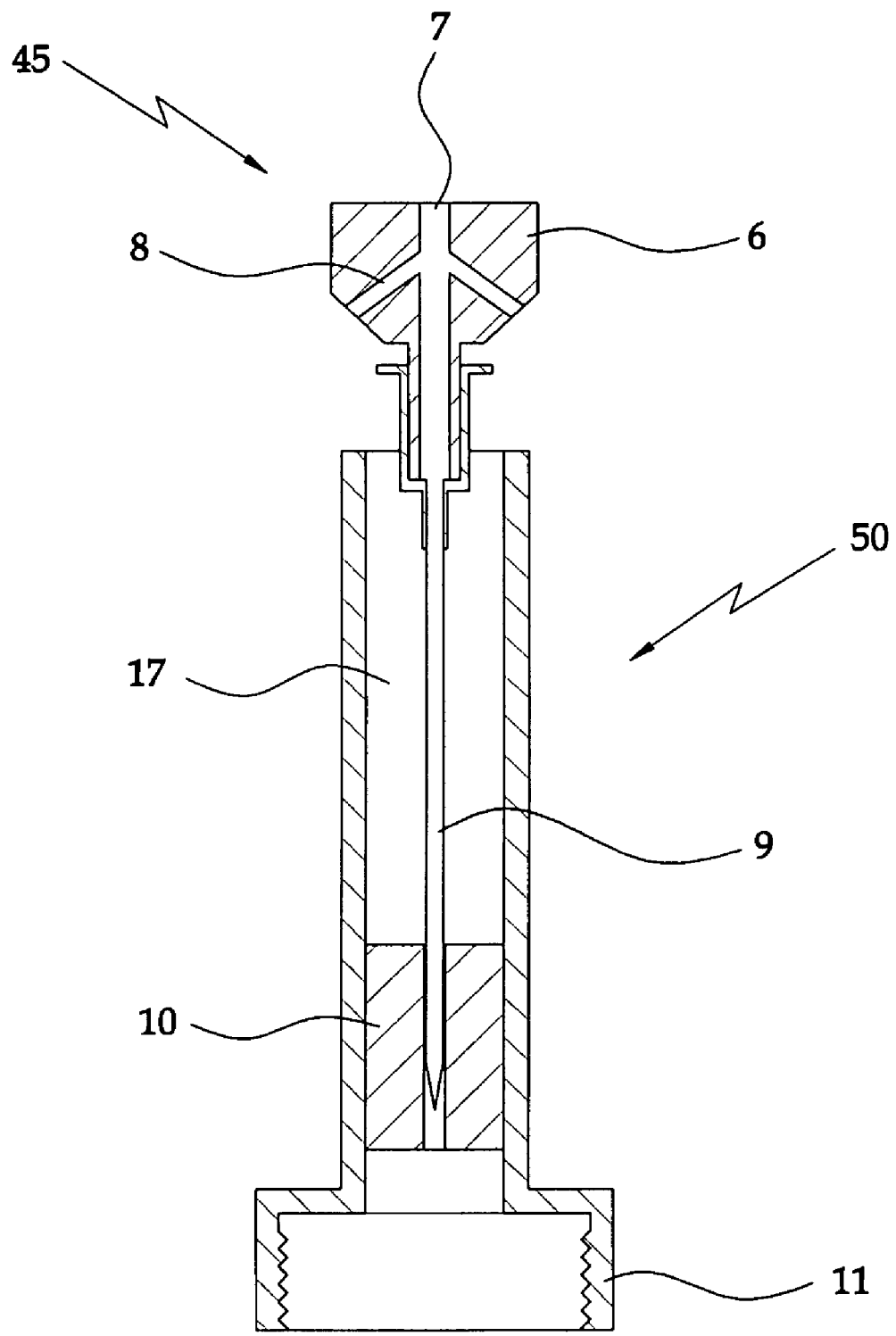
FIG. 11a is schematic view showing a state of the sampling needle part and the guiding part before operation.
Figure 11B:
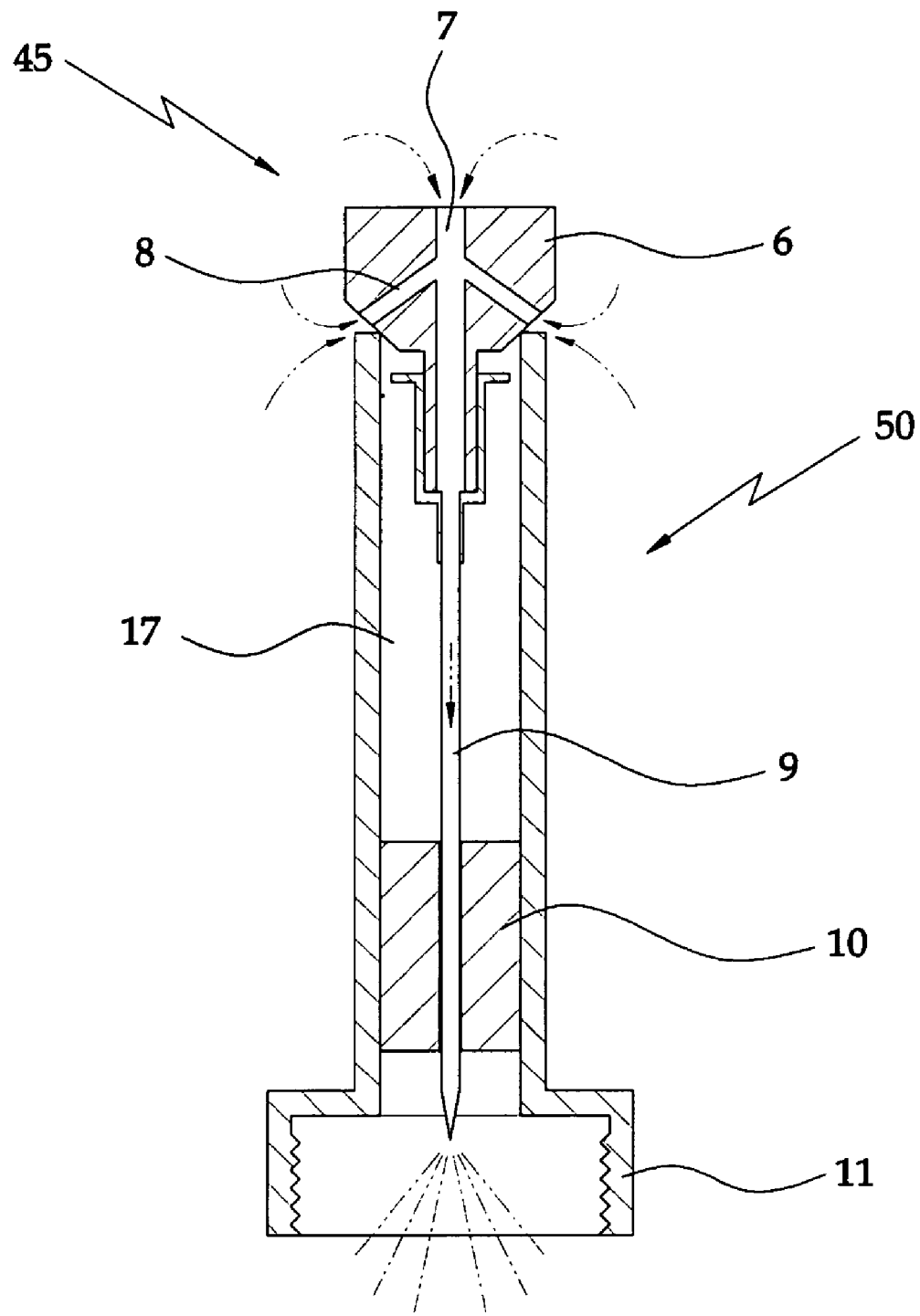
FIG. 11b is schematic view showing a state of the sampling needle part and the guiding part after operation.

FIG. 10 is a schematic view showing an assembled sate of the sampling needle part 45, the guiding part 50, and the sampled water containing part 60 according to an embodiment of the present invention. FIG. 11a is schematic view showing a state of the sampling needle part 45 and the guiding part 50 before operation. FIG. 11b is a schematic view showing a state of the sampling needle part 45 and the guiding part 50 just after operation. In the figures, the size of the circumference of the impacting part 6 in the sampling needle part 45 is larger than that of the guide 17 in the guiding part 50, thereby defining the falling and impacting movement of the sampling needle part 45.

The size of the impacting part 6 is larger than the guide 17 so that the side suction hole 8 is positioned at a higher elevation with respect to the uppermost surface of the guide 17. In this manner, a sample of groundwater can be injected into the needle 9 while the impacting part 6 of the sampling needle part 45 is in contact with the upper end of the guide 17 of the guiding part 50.

Operation of the illustrated embodiment of present invention will now be described in detail.

One end of the sampled water container 14 is sealed with the rubber packing 12, air in the sampled water container 14 is removed by a vacuum pump to make the sampled water container 14 vacuous, the guiding part 50 (for guiding the vertical falling movement of the needle 9) is connected to the upper end of the sampled water container 14 sealed with the packing 12, and the sampling needle part 45 having the needle 9 mounted thereon is positioned on the upper end of the guiding part 50.

The impacting part 6 formed on the upper end of the sampling needle part 45 is positioned coaxially with the hammer 5 of the hammer part 40.

The hammer 5 performs rising and falling movement by the elasticity of the spring 4 mounted thereon.

In some applications, a number of individual devices for discrete interval groundwater sampling according to the present invention are connected with one another. That is, the upper connecting ring 1 formed on the uppermost end of the hammer part 40 in a first device and the lower connecting ring 15 formed on the lowermost end of the sampled water containing part 60 in any other device under the first device are connected mutually by a steel wire, with a regular interval according to a target depth, and the uppermost device is connected to a wire drum by a steel wire.

Then, the connected devices are dropped down to a target depth in a borehole through a tripod having a pulley, after which a waiting period of time elapses in order to stabilize the flow state of the groundwater. After the flow of the groundwater is in a stable state, the steel wire connected to the device is lifted up by about 1 m, and is dropped in a free fall.

The device undergoes free fall by the length by which the device is lifted up to stop. At this time, the hammer 5 connected to the spring 4 moves in a straight motion by means of an inertial force, and the needle 9 which is impacted by the straight-line motion of the hammer 5 is passed through the packing 12 of the sampled water container 14 through the guiding part 50 (which guides the straight-line motion of the needle 9 and is positioned on the upper end of the sampled water container 14).

At this moment, as the pressure in the sampled water container 14 is lower than that of the surrounding groundwater, the groundwater flows into the needle 9 through the upper and the side suction holes 7 and 8 formed on the upper part of the sampling needle part 45.

The groundwater is stored in the sampled water container 14 via the needle 9, which was passed through the packing 12 of the sampled water container 14. It takes about 20 minutes in order to fully store the sampled water container 14 with the groundwater (at a height of 50 cm in the sampled water container 14). It is possible to sample the groundwater for each of two or more determined intervals, as the procedures described above for sampling groundwater can be applied simultaneously to each of other devices positioned on the target depths.

A method for sampling groundwater by using a device for discrete interval groundwater sampling according to an embodiment the present invention will now be described in detail.

The method is comprised of: making the sampled water container 14 in the sampled water containing part 60 vacuous by removing air in the sampled water container 14 by a vacuum pump; positioning each of the devices for desired target depths; lifting up the steel wire connecting the devices by 1 m, and permitting the devices to free fall; impacting the impacting part 6 of the sampling needle part 45 with the hammer 5 connected to the lower end of the spring 4 in the hammer part 40 through the inertial force of the hammer 5 after the device performs the free fall; moving the needle 9 in the sampling needle part 45 impacted by the hammer 5 down through the needle guide 10; filling the needle 9 with a sample of water through the upper and side suction holes 7 and 8 in the sampling needle part 45; and penetrating the needle through the packing of the sampled water containing part 60 to inject a sample of water into the sampled water container 14.

By describing in detail, the air in the sampled water container 14 is first removed by a vacuum pump in order to increase the flow rate of the groundwater into the sampled water container 14 and the amount of the groundwater received within the sampled water container 14. The sampled water container 14 is then installed on the device.

Next, the length of the steel wire connecting the devices with each other is adjusted so as to arrange the devices to desired target depths to sample groundwater according to the target depths, the devices are connected to the steel wire, the devices are lowered down in the borehole, and a period of time is waited for a stable state of the groundwater (disturbed by the lowering of the devices) to be reached. After this, the wire is lifted up by 1 m, one end of the steel wire is fixed, and the device is permitted to free fall.

The device undergoes free fall by the length by which the device is lifted up to stop. At this time, the hammer 5 connected to the spring 4 moves in a straight motion by means of an inertial force, and the needle 9 which is impacted by the straight-line motion of the hammer 5 is passed through the packing 12 of the sampled water container 14 through the guiding part 50 (which guides the straight-line motion of the needle 9 and is positioned on the upper end of the sampled water container 14).

At this moment, as the pressure in the sampled water container 14 is lower than that of the surrounding groundwater, the groundwater flows into the needle 9 through the upper and the side suction holes 7 and 8 formed on the upper part of the sampling needle part 45.

The groundwater is stored in the sampled water container 14 via the needle 9, which was passed through the packing 12 of the sampled water container 14. It takes about 20 minutes in order to fully store the sampled water container 14 with the groundwater (at a height of 50 cm in the sampled water container 14). It is possible to sample the groundwater for each of two or more determined intervals, as the procedures described above for sampling groundwater can be applied simultaneously to each of other devices positioned on the target depths.

When pulling up the devices to ground level, the groundwater which is at other target depths in the pulling-up direction does not flow into each sampled water container 14 of the devices, as the pressure in the sampled water container 14 is higher than that of the groundwater in the pulling-up direction.

It is possible to separate the sampled water container 14 from the devices pulled up to ground level, and to carry the separated container 14 to a laboratory or an analytical laboratory without exposing the groundwater sample to air. Further, it is possible to reuse the sampled water container 14 after washing the sampled water container 14. Also, it is possible to sample groundwater in a desired amount, as the volume of the sampled water container 14 is adjustable.

As described above, the effect of the devices and methods for sampling groundwater for multiple target depths is as follows.

It is possible to sample groundwater at multiple target depths without any driving source, such as an electrical or pneumatic driving source. The devices according to some embodiments of the present invention are appropriate in applications where groundwater must be sampled in a borehole simultaneously at multiple target depths. Further, the cost of fabricating the devices is lower, as a driving source is not required. In addition, from a time and commercial point of view, the present invention is very effective compared to conventional devices that are employed to sample groundwater in a number of boreholes.

Further, every part forming the present invention can be easily separated, and can be reused through washing. In particular, in the case of sampling groundwater at deeper depths, it is not required to make the sampled water container vacuous, since the groundwater will be at higher pressures at deeper depths.

Further, some embodiments of the present invention aim at providing devices for sampling groundwater for multiple target depths, in which it is possible to sample groundwater by a desired amount (as the volume of the sampled water container 14 is adjustable), and in which the user is not limited to a particular sampling depth (as the deeper the depth is, the higher the pressure of the groundwater is).

The invention claimed is:

1. Devices for sampling groundwater at multiple target depths, wherein one end of a first of the devices is connected to a first steel wire and the devices are connected with each other through second steel wires, each of the devices comprising:
    a hammer part having a spring and a hammer, said hammer part generating inertial force;
    a sampling needle part having a needle integral with an impacting part, said impacting part impacting against the hammer;
    a guiding part for moving straight down the sampling needle part; and
    a sampled water containing part having a sampled water container, said sampled water container receiving a sampled water injected from the needle, said needle being moved down in the guiding part.

2. The devices as claimed in claim 1, wherein the hammer part further comprises a position adjusting bolt, the spring is connected to a lower end of the position adjusting bolt, and the hammer is connected to a lower end of the spring.

3. The devices as claimed in claim 1, further comprising a hammer casing for free movement of the hammer by minimizing resistance caused by groundwater, said hammer casing formed as a tube to position the hammer part therein for protecting the hammer part, and having at least two passages for sampling formed on a circumference thereof for flow of groundwater when the hammer is moved up and down.

4. The devices as claimed in claim 2, wherein the hammer part further comprises a position adjusting screw provided for the inertial force and a position of the hammer in the position adjusting bolt.

5. The devices as claimed in claim 2, further comprising a hammer casing for free movement of the hammer by minimizing resistance caused by groundwater, said hammer casing formed as a tube to position the hammer part therein for protecting the hammer part, and having at least two passages for sampling formed on a circumference thereof for flow of groundwater when the hammer is moved up and down.

6. The devices as claimed in claim 4, further comprising a hammer casing for free movement of the hammer by minimizing resistance caused by groundwater, said hammer casing formed as a tube to position the hammer part therein for protecting the hammer part, and having at least two passages for sampling formed on a circumference thereof for flow of groundwater when the hammer is moved up and down.

7. The devices as claimed in claim 1, wherein the sampling needle part further comprises an upper suction hole formed on an upper surface of the impacting part impacting against the hammer, wherein the needle is vertically connected and communicated to and with the upper suction hole.

8. The devices as claimed in claim 7, wherein the sampling needle part further comprises a side suction hole, said side suction hole formed on a side surface of the impacting part and communicated with the upper suction hole.

9. The devices as claimed in claim 8, further comprising a casing for the sampling needle part connected to a lower end of a hammer casing, said casing for the sampling needle part being formed as a tube to position the sampling needle part therein for protecting the sampling needle part, and having at least one passage for sampling formed on a circumference thereof to permit flow of sampled water therein.

10. The devices as claimed in claim 7, further comprising a casing for the sampling needle part connected to a lower end of a hammer casing, said casing for the sampling needle part being formed as a tube to position the sampling needle part therein for protecting the sampling needle part, and having at least one passage for sampling formed on a circumference thereof to permit flow of sampled water therein.

11. The devices as claimed in claim 1, wherein said guiding part further comprises:
   a guide shaped as a tube;
   a needle guide positioned on a lower end of the guide and conducting vertical downward movement of the sampling needle; and
   a guide locking portion connected to the lower end of the guide, said guide locking portion adjusting a degree that the needle penetrates through a rubber packing.

12. The devices as claimed in claim 1, wherein the sampled water containing part further comprises:
   a submerging part having a shape corresponding to a guide locking portion of the guiding part and being hollow; and
   a packing part mounted on an upper end of the submerging part;
   wherein the sampled water container contains a sampled groundwater, and is connected to a lower end of the submerging part.

13. The devices as claimed in claim 12, wherein the packing part is formed with an elastic rubber to close up the sampled water containing part.

14. The devices as claimed in claim 1, further comprising an upper connecting ring connected to an upper end of the hammer part.

15. The devices as claimed in claim 1, further comprising a lower connecting ring connected to a lower end of the sampled water containing part.

16. The devices as claimed in claim 1, wherein a circumference of the impacting part in the sampling needle part is formed larger than that of a guide in the guiding part to define falling-down and impacting movement of the sampling needle part.

17. The devices as claimed in claim 1, wherein a side suction hole is positioned relatively higher than a guide of the guiding part to suck a sample of water in the side suction hole so as to inject surrounding sampling groundwater into the sampling needle when the impacting part in the sampling needle part is impacted with the guide in the guiding part.

* * * * *